United States Patent [19]

Koller et al.

[11] Patent Number: 4,844,841
[45] Date of Patent: Jul. 4, 1989

[54] PYRENEXULFONIC ACIDS USEFUL IN FLUORESCENT LIPID PROBES

[76] Inventors: Ernst Koller, Kirchbach 8, 8082 Kirchbach; Otto S. Wolfbeis, Im Hoffeld 32, 8046 Graz, both of Austria

[21] Appl. No.: 96,043

[22] Filed: Sep. 11, 1987

[30] Foreign Application Priority Data

Jun. 13, 1986 [AT] Austria .................................. 1604/86

[51] Int. Cl.⁴ .................... C07C 143/38; C07C 143/56
[52] U.S. Cl. ...................................... 562/55; 260/509; 260/512 C; 546/347; 558/408; 558/410; 558/413; 560/14; 562/71; 562/72; 562/76; 562/77
[58] Field of Search .................... 260/508, 509, 512 C; 560/14; 558/408, 410, 413; 546/347

[56] References Cited

U.S. PATENT DOCUMENTS 2,094,224 9/1937 Tietze et al. ..................... 260/512 C Primary Examiner—Nicky Chan
Attorney, Agent, or Firm—Hill, Van Santen, Steadman & Simpson

[57] ABSTRACT

Compounds of formula

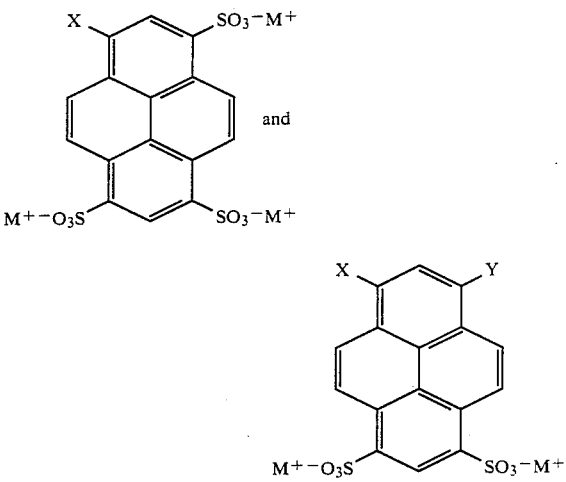

wherein
 X is long-chain alkyloxy, long-chain alkylamino or long-chain dialkylamino,
 M is alkali metal, pyridinium or ammonium;
 Y is hydroxy or long-chain alkyloxy,
which are especially useful in photometric and fluorimetric investigations of lipids and lipid-water interactions and of cationic biomolecules such as nicotine adenine dinucleotide.

17 Claims, 2 Drawing Sheets

PYRENEXULFONIC ACIDS USEFUL IN FLUORESCENT LIPID PROBES

The invention is related to a new class of lipid probes that can be used in lipid chemistry and analytical biochemistry.

Fluorescent lipid probes have frequently been used in the last years in order to study membranes, micelles, vesicles and lipid-water interfaces (Fluorescent Probes, G. S. Beddard and M. A. West (ed.), Academic Press, New York, 1981). In essence these probes consist of a lipid chain to which a fluorophore is attached. The lipid chain provides the compatibility with the lipid phase, whereas the fluorophore acts as a reporter for the microenvironment. Thus from the effect of a changing microenvironment or pH on the spectral properties of the fluorophore, conclusions can be made as to the microenvironment that surrounds the fluorescent probe.

A number of lipid probes has so far been reported in the literature, but only a few have been found to be useful in practice. Typical examples include (9-anthroyloxy)stearic acids (L. Tilley et al. (1979) J. Biol. Chem. 254, 2592). Another useful probe is 1,6-diphenyl-1,3,5-hexatriene (DPH), which shows a polarity- and viscosity-dependent fluorescence (G. S. Beddard and M. A. West, loc. cit.). Another group comprises the (1-pyrene)fatty acids which have also found widespread use (C. Lovejoy et al. (1977) Biochemistry 16, 3668). Most of the probes reported so far have properties that limit their applications. Thus most probes have short-wave excitation and emission wavelengths so that the strong background fluorescence from biological materials can interfere heavily. Second, probes such as DPH are photolabile. And practically all fluorescent probes have inproper water solubility and suffer from fluorescence quenching by oxygen. We describe here a new group of fluorescent probes that have longwave excitation and emission, high fluorescence quantum yields, good water solubility and no sensitivity to oxygen. The probes are derived from fluoropohores whose chemical structure are given in structure I, II, and III.

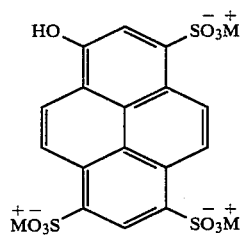

I

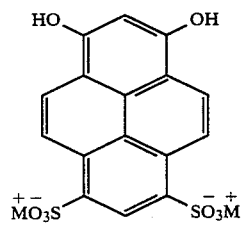

II

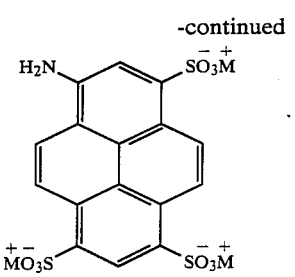

III

These fluorophores can be chemically linked to long alkyl chains to give a new class of lipid probes that is characterized by an apolar lipid chain and a highly polar fluorophore (structures IV, V, VI, and VII).

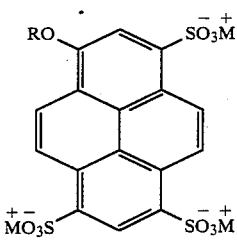

IV

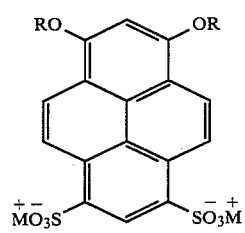

V

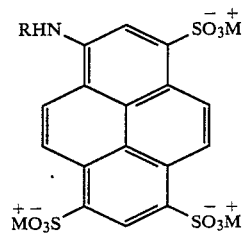

VI

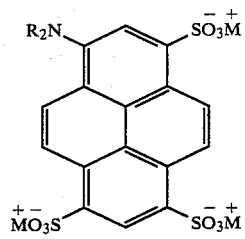

VII

The substituent R in structure IV, V, VI and VII can be an alkyl, alkenyl, arylalkenyl or arylalkyl group comprising 4–22 carbon atoms, which can be substituted by carboxy, alkoxycarbonyl, cyano, hydroxy, chlorine, bromine, or sulfonato groups. Typical substituents include the decyl, dodecyl, tetradecyl, hexydecyl, octadecyl group and their omega carboxy derivatives. Suitable cations in structure IV, V, VI, and VII are sodium, potassium, ammonium, or pyridinium. Sodium and pyridinium ions are prefered.

Another group of new lipid probes comprises compounds of chemical structure VIII, IX, and X

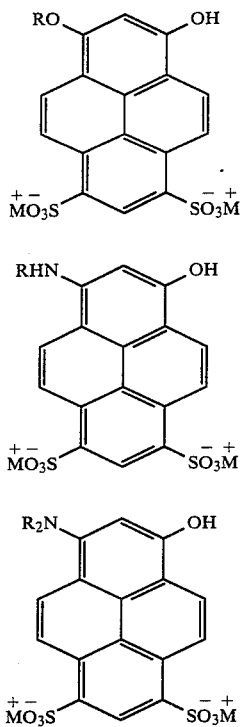

where R and M have the same meaning as in structures IV, V, VI, and VII.

Compounds of general formula IV–VII can be obtained by reaction of proper alkyl halides of structure R—X, or dialkylsulfates of structure RO—SO$_2$—OR, or alkyltoluenesulfonates of structure RO—SO$_2$—C$_6$H$_4$—CH$_3$, with phenols of structures I or II, or an amine of structure III. Reaction is preferentially performed in the presence of an inorganic or organic base at temperatures between 0°–180° C. in a solvent such as ethanol, dimethylformamide, or dimethylsulfoxide, or their mixtures with water. Prefered bases are pyridine, or dissolved or suspended alkali hydroxides or alkali carbonates.

Compounds of structures VIII, IX, and X are obtained from lipid probes of type IV, VI and VII by reaction with an alkali hydroxide at temperatures between 50°–200° C.

Probes IV, VI and VII can be obtained by sulfonation of pyrenes of structure XI, XII, or XIII

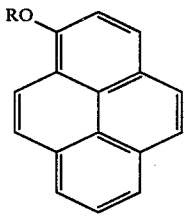

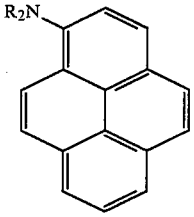

where R has the same meaning as in compounds IV–VII, with a sulfonating agent such as sulfuric acid or oleum.

Figure 1:
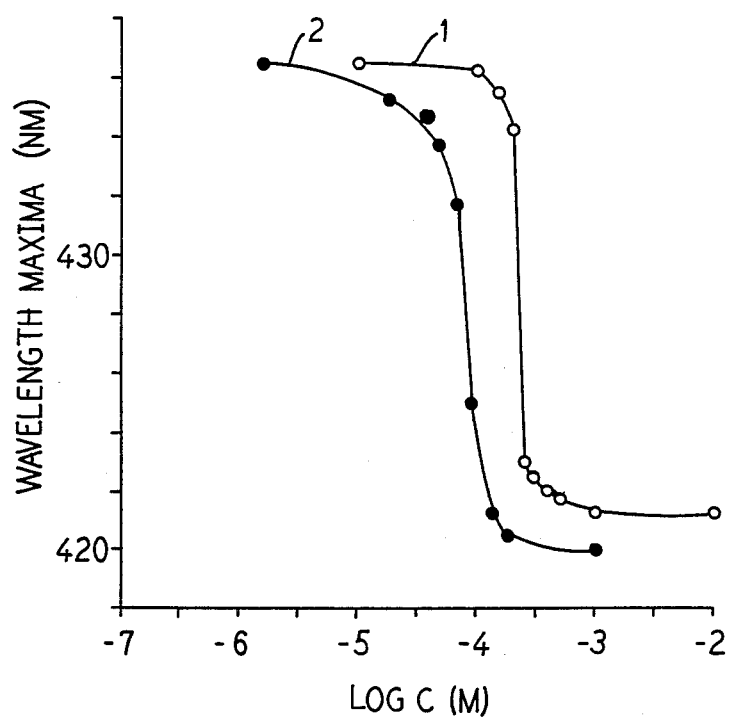
FIG. 1 shows the fluorescence maxima as a function of the detergent concentration c.
Figure 2:
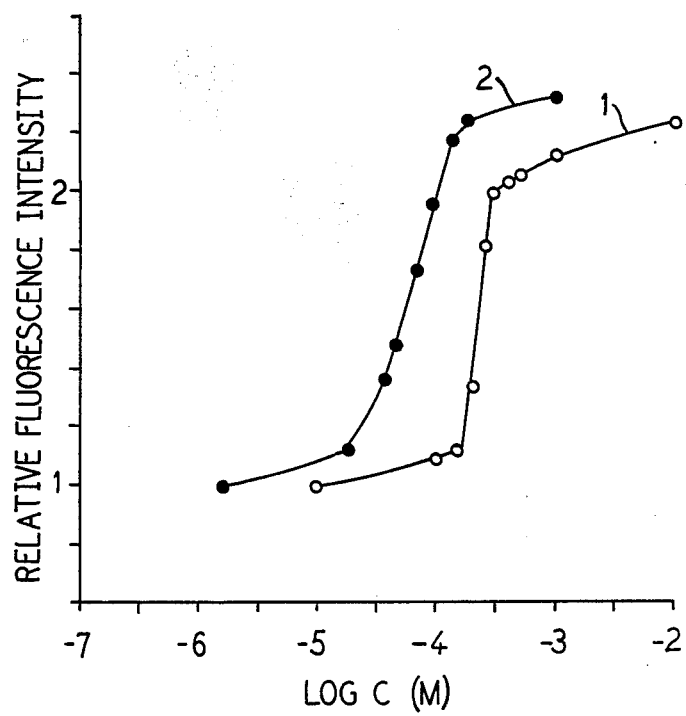
FIG. 2 shows the relative fluorescence intensity as a function of the detergent concentration c.

The lipid probes of general formula IV–X have excellent water solubility because of the presence of polar sulfonato groups. Due to an unique combination of a polar fluorophore group and an apolar lipid chain the probes are most suitable for investigating lipid-water systems such as micelles, vesicles, membranes, and lipid-water interfaces. Usually the polar group is exposed to the aqueous phase and the alkyl chain is anchored in the lipid domaine. Typical probe applications include the determination of critical micelle concentration (cmc) and of lipid polarity and viscosity. FIG. 1 shows the effect of detergent concentration c (1, Triton X-100; 2, Brij-35) on the fluorescence maximum. The probe used in this experiment is 1-decyloxypyrene-3,6,8-trisulfonate. It is obvious, that at the cmc of Triton X-100 ($2.2 \cdot 10^{-4}$M, curve 1) and Brij-35 ($6.6 \cdot 10^{-5}$M, curve 2) a significant change in the emission maximum occurs. Similarly, the emission intensity, measured at 420 nm can be used to determine the cmc. FIG. 2 shows that there is a dramatic increase in relative fluorescence intensity when the concentration of detergents Triton X-100 (curve 1) or Brij-35 (curve 2 ) exceeds the cmc.

Aminopyrenes of structure VI and VII have applications similar to alkoxypyrenes IV and V but have even longer excitation and emission wavelengths (450/510 nm).

Probes of structure VIII–X are useful for determination of physiological pH values since the pK$_a$ of the hydroxy group is between 6.5 and 8.5. At pH values above the pK$_a$ value, they form a highly fluorescent phenolate anion with particular longwave excitation and emission (460/520 nm) that is highly pH-dependent. Because of the long chain alkyl substituent R the probes bind to the lipid membranes and therefore lends themselves to pH determination at membrane surfaces.

Figure 3:
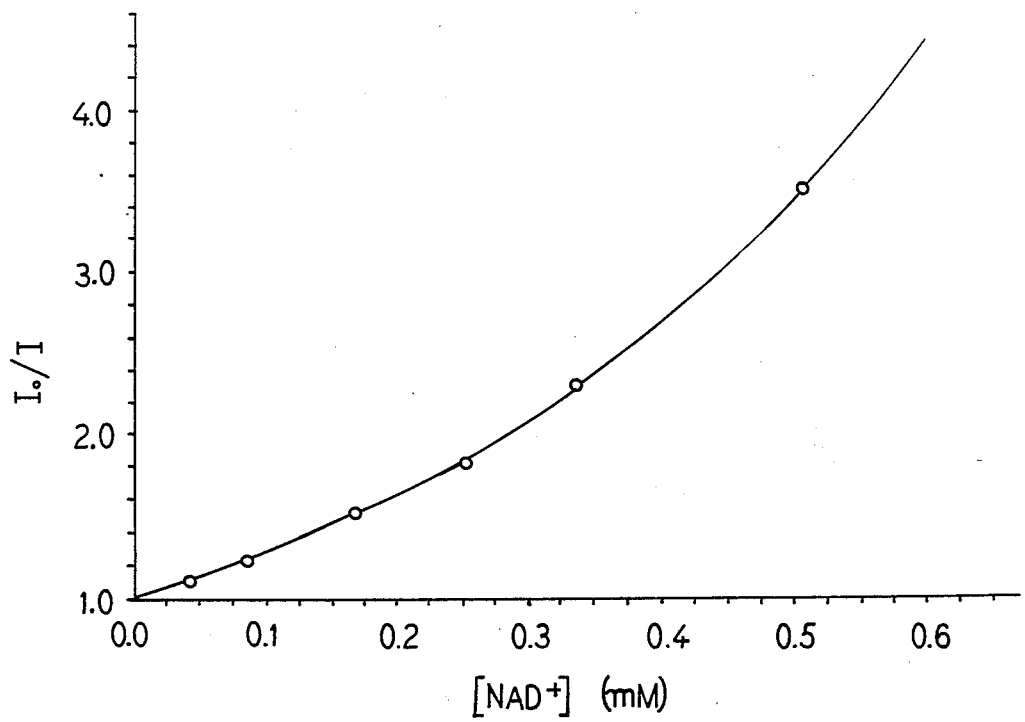
FIG. 3 shows the fluorescence intensity as a function of the MAD+ concentration.

An unexpected observation is the fact that lipid probes IV–X suffer fluorescence quenching by cationic biomolecules such as nicotine adenine dinucleotide (NAD+) and its phosphate (NADP+), by vitamin B1 and other cations such as cetylpyridiniumchloride (CPC). A Stern-Volmer plot of the quenching of 1-octadecyloxypyrene-3,6,8-trisulfonate by NAD+ is shown in FIG. 3, where the ratio of $I_o/I$ (i.e., the fluorescence intensity of probe 1-octadecyloxypyrene-3,6,8-trisulfonate) is plotted versus the concentration of NAD+. $I_o$ is the fluorescence intensity of the probe in the absence of NAD+, and I is the intensity of the probe in the presence of a certain concentration [NAD+]. The curve can be described by a modified Stern-Volmer equation of type $$I_o/I=(1+K_d\cdot[Q])\cdot e^{v\cdot[Q]}$$

as described by J. R. Lakowicz in: "Principles of Fluorescence Spectroscopy", Plenum Press, New York, 1983, p 266 ff. Here, $I_o$ and I have the same the same meaning as in FIG. 3, the quencher Q is NAD+ being presnt in a concentration [NAD+] (in millimol), $K_d$ is the dynamic quenching constant, and v in the exponential term accounts for static quenching. Solving the equation by using the experimental data shows that the dynamic quenching term $K_d$ is negligibly small (0.1), but that static quenching is predominant. The experimental value for v is as high as $2,480 M^{-1}$.

Because of the unambiguous relation between fluorescence intensity and NAD+ concentration (FIG. 3), the probes are suitable for quantitative determination of NAD+ and other cationic species, and also for monitoring biochemical reactions during which these species are produced or consumed.

EXAMPLES

Example 1

1-Decyloxypyrene-3,6,8-trisulfonic acid trisodium salt (structure IV, R=decyl, M=Na).

7.5 g (34 mmol) decylbromide are added to a mixture of 2.0 g (3.8 mmol) 1-hydroxypyrene-3,6,8-trisulfonic acid trisodium salt (compound I, M=Na) and 4.0 g (38 mmol) sodium carbonate in a mixture of 40 ml dimethylformamide and 10 ml water and heated under reflux for 6 h under stirring. Volatile solvents are removed in a vacuum at 100° C. Then, 100 ml acetone are added. The grey material is filtered off, washed with acetone and recrystallized from 90% ethanol under addition of charcoal. The decylether is obtained in 75% yield (1.9 g) as yellowish needles that decompose at 245° C.

In a similar fashion, the dodecylether (decomposition at 260° C.) and the octadecylether (decomposition at 243° C.) are obtained.

When 1,3-dihydroxypyrene-6,8-disulfonic acid disodium salt (compound II, M=Na) is used in place of compound I in the preceding procedure, lipid probes of structure V (M=Na) are obtained. Typical examples are the bis-dodecylether (structure V, R=n-dodecyl, M=Na) of melting point 202° C. and the bis-octadecylether (structure V, R=n-octadecyl, M=Na) of melting point 234° C.

Example 2

1-Decyloxy-3-hydroxypyrene-6,8-disulfonic acid disodium salt (structure VIII, R=decyl, M=Na).

14.5 g Sodium hydroxide and 9.0 g water are heated to ca. 130° C. and 8.53 g 1-decyloxypyrene-3,6,8-trisulfonate (structure IV, R=decyl, M=Na) are added to the melt in small portions under stirring. The temperature is raised within 30 min to 190° C. The mixture is cooled, cautiously acidified with concentrated hydrochloric acid, and the resulting precipitate is filtered and recrystallized from a saturated aqueous salt solution. For further purification it is recrystallized from aqueous ethanol. Yield is 2.6 g of yellow crystals that decompose at above 232° C. and which have a green fluorescence that is strongly pH-dependent in the pH 6-8 range.

Example 3

N,N-Didodecyl-1-aminopyrene-3,6,8-trisulfonic acid trisodium salt (structure VII, R=dodecyl, M=Na).

2.0 g of N,N-Di-dodecyl-1-aminopyrene are added in small portions to a solution of 1.5 g sodium sulfate in 6.5 g concentrated sulfuric acid. To this mixture, 4.0 g of oleum ($SO_2$ content 65%) is added dropwise at 60° C. under stirring. After standing for 12-20 h, the mixture is carefully poured on ice and cautiously neutralized with concentrated sodium hydroxide. The solution is evaporated to dryness and the solid residue extracted with 150 ml methanol. After evaporating the methanol, the residue is crystallized, first from saturated salt solution, then from aqueous ethanol. Yield 1.7 g of brownish-yellow material that decomposes at 205° C. When excited with 450 nm light, the probe displays a strong green fluorescence with a maximum at 508 nm.

We claim:
1. A compound having the formula

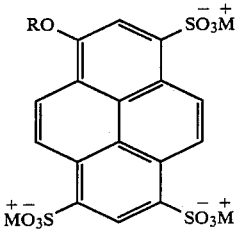

wherein
R is a radical consisting of 4–22 carbon atoms chosen from the group consisting of alkyl, alkenyl and arylalkenyl, which can be substituted by carboxy, alkoxycarbonyl, hydroxy, cyano, chlorine, bromine or sulfonato groups; and
M is chosen from the group consisting of alkali metal, pyridinum or ammonium.

2. A compound having the formula

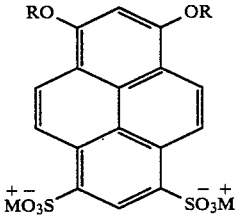

wherein
R is a radical consisting of 4–22 carbon atoms chosen from the group consisting of alkyl, alkenyl and arylalkenyl, which can be substituted by carboxy, alkoxycarbonyl, hydroxy, cyano, chlorine, bromine or sulfonato groups; and
M is chosen from the group consisting of alkali metal, pyridinum or ammonium.

3. A compound having the formula

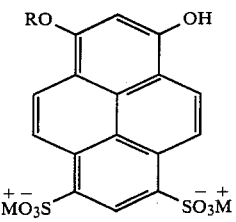

wherein
R is a radical consisting of 4–22 carbon atoms chosen from the group consisting of alkyl, alkenyl and arylalkenyl, which can be substituted by carboxy, alkoxycarbonyl, hydroxy, cyano, chlorine, bromine or sulfonato groups; and
M is chosen from the group consisting of alkali metal, pyridinum or ammonium.

4. A compound having the formula

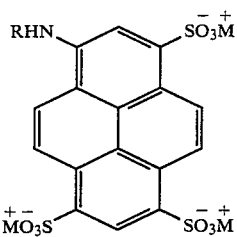

wherein
R is a radical consisting of 4–22 carbon atoms chosen from the group consisting of alkyl, alkenyl and arylalkenyl, which can be substituted by carboxy, alkoxycarbonyl, hydroxy, cyano, chlorine, bromine or sulfonato groups; and
M is chosen from the group consisting of alkali metal, pyridinum or ammonium.

5. A compound having the formula

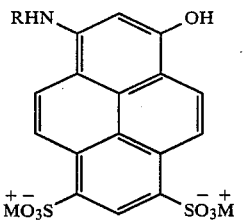

wherein
R is a radical consisting of 4–22 carbon atoms chosen from the group consisting of alkyl, alkenyl and arylalkenyl, which can be substituted by carboxy, alkoxycarbonyl, hydroxy, cyano, chlorine, bromine or sulfonato groups; and
M is chosen from the group consisting of alkali metal, pyridinum or ammonium.

6. The compound of claim 1 wherein R is chosen from the group consisting of decyl, dodecyl, tetradecyl, hexadecyl, octadecyl, 10-carboxy-decyl, 14-carboxy-tetradecyl, 10-ethoxycarbonyl-decyl, 14-methoxycarbonyl-tetradecyl, 10-chloro-decyl, 12-bromo-dodecyl, 12-hydroxy-dodecyl, 14-hydroxy-tetradecyl radical and M is sodium.

7. A compound have the formula

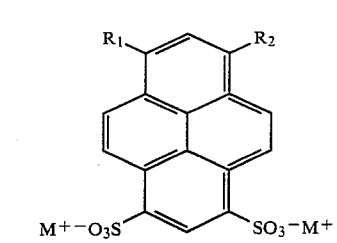

wherein
$R_1$ is a radical consisting of 4–22 carbon atoms chosen from the group consisting of alkyloxy, alkenyloxy, arylalkyloxy, alkylamino, alkenyl-amino, dialkylamino, and dialkenylamino radical which can be substituted by carboxy, alkoxycarbonyl, hydroxy, cyano, chlorine, bromine, or sulfonato groups;
$R_2$ is a hydroxy or sulfonato group; and
M is chosen from the group consisting of alkali metal, pyridinium, and ammonium.

8. The compound of claim 7 wherein:
$R_1$ is chosen from the group consisting of decyloxy, dodecyloxy, tetradecyloxy, hexadecyloxy, octadecyloxy, 10-carboxy-decyloxy, 14-carboxy-tetradecyloxy, 10-ethoxycarbonyldecyloxy, 14-methoxycarbonyl-tetradecyloxy, 12-bromododecyloxy, and 14-hydroxy-tetradecyloxy radical; and
M is sodium.

9. The compound of claim 7 wherein:
$R_1$ is chosen from the group consisting of a decylamino, didecylamino, dodecylamino, didodecylamino, tetradecylamino, ditetradecylamino, hexadecylamino, dihexadecylamino, bis(10-carboxydecyl)amino, and bis(12-carboxydodecyl)amino radical; and
M is sodium.

10. A compound having the formula

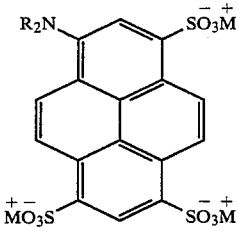

wherein
R is a radical consisting of 4–22 carbon atoms chosen from the group consisting of alkyl, alkenyl and arylalkenyl, whch can be substituted by carboxy, alkoxycarbonyl, hydroxy, cyano, chlorine, bromine or sulfonato groups; and
M is chosen from the group consisting of alkali metal, pyridinum or ammonium.

11. A compound having the formula

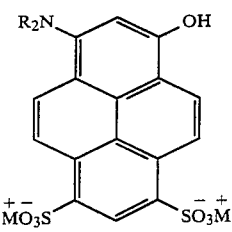

wherein
R is a radical consisting of 4–22 carbon atoms chosen from the group consisting of alkyl, alkenyl and arylalkenyl, which can be substituted by carboxy, alkoxycarbonyl, hydroxy, cyano, chlorine, bromine or sulfonato groups; and
M is chosen from the group consisting of alkali metal, pyridinum or ammonium.

12. The compound of claim 2 wherein R is chosen from the group consisting of decyl, dodecyl, tetradecyl, hexadecyl, octadecyl, 10-carboxy-decyl, 14-carboxy-tetradecyl, 10-ethoxycarbonyl-decyl, 14-methoxycarbonyl-tetradecyl, 10-chlorodecyl, 12-bromo-dodecyl, 12-hydroxy-dodecyl, 14-hydroxy-tetradecyl radical; and M is sodium.

13. The compound of claim 3 wherein R is chosen from the group consisting of decyl, dodecyl, tetradecyl, hexadecyl, octadecyl, 10-carboxy-decyl, 14-carboxy-tetradecyl, 10-ethoxycarbonyl-decyl, 14-methoxycarbonyl-tetradecyl, 10-chlorodecyl, 12-bromo-dodecyl, 12-hydroxy-dodecyl, 14-hydroxy-tetradecyl radical; and M is sodium.

14. The compound of claim 4 wherein R is chosen from the group consisting of decyl, dodecyl, tetradecyl, hexadecyl, octadecyl, 10-carboxy-decyl, 14-carboxy-tetradecyl, 10-ethoxycarbonyl-decyl, 14-methoxycarbonyl-tetradecyl, 10-chlorodecyl, 12-bromo-dodecyl, 12-hydroxy-dodecyl, 14-hydroxy-tetradecyl radical; and M is sodium.

15. The compound of claim 5 wherein R is chosen from the group consisting of decyl, dodecyl, tetradecyl, hexadecyl, octadecyl, 10-carboxy-decyl, 14-carboxy-tetradecyl, 10-ethoxycarbonyl-decyl, 14-methoxycarbonyl-tetradecyl, 10-chlorodecyl, 12-bromo-dodecyl, 12-hydroxy-dodecyl, 14-hydroxy-tetradecyl radical; and M is sodium.

16. The compound of claim 10 wherein R is chosen from the group consisting of decyl, dodecyl, tetradecyl, hexadecyl, octadecyl, 10-carboxy-decyl, 14-carboxy-tetradecyl, 10-ethoxycarbonyl-decyl, 14-methoxycarbonyl-tetradecyl, 10-chlorodecyl, 12-bromo-dodecyl, 12-hydroxy-dodecyl, 14-hydroxy-tetradecyl radical; and M is sodium.

17. The compound of claim 11 wherein R is chosen from the group consisting of decyl, dodecyl, tetradecyl, hexadecyl, octadecyl, 10-carboxy-decyl, 14-carboxy-tetradecyl, 10-ethoxycarbonyl-decyl, 14-methoxycarbonyl-tetradecyl, 10-chlorodecyl, 12-bromo-dodecyl, 12-hydroxy-dodecyl, 14hydroxy-tetradecyl radical; and M is a sodium.

* * * * *

UNITED STATES PATENT AND TRADEMARK OFFICE
CERTIFICATE OF CORRECTION

PATENT NO. : 4,844,841
DATED : July 4, 1989
INVENTOR(S) : Ernst Koller et al

It is certified that error appears in the above—identified patent and that said Letters Patent is hereby corrected as shown below:

In the title, "PYRENEXULFONIC" should read - - PYRENESULFONIC - -.

Signed and Sealed this

Tenth Day of April, 1990

Attest:

HARRY F. MANBECK, JR.

*Attesting Officer*   *Commissioner of Patents and Trademarks*